(12) United States Patent
Hubert et al.

(10) Patent No.: US 6,586,255 B1
(45) Date of Patent: *Jul. 1, 2003

(54) AUTOMATED CENTRIFUGE LOADING DEVICE

(75) Inventors: Ronald M. Hubert, Yardley, PA (US); Rodney D. Miller, West Chester, PA (US)

(73) Assignee: Quest Diagnostics Incorporated, Teterboro, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/111,898

(22) Filed: Jul. 8, 1998

Related U.S. Application Data
(60) Provisional application No. 60/053,260, filed on Jul. 21, 1997.

(51) Int. Cl.[7] ................................................ G01N 35/00
(52) U.S. Cl. ............................ 436/45; 436/43; 436/47; 436/48; 436/174; 436/180; 422/63; 422/64; 422/65; 422/72; 422/102; 422/104

(58) Field of Search .............................. 436/43, 45, 47, 436/48, 174, 180; 422/63, 64, 65, 72, 102, 104

(56) References Cited

U.S. PATENT DOCUMENTS 4,735,776 A * 4/1988 Yamamoto et al. ........... 422/65
5,122,343 A * 6/1992 Ishizaka et al. ............... 422/66
5,578,269 A * 11/1996 Yaremko et al. .............. 422/64

FOREIGN PATENT DOCUMENTS

EP 0629858 * 12/1994

* cited by examiner

Primary Examiner—Jill Warden
Assistant Examiner—Kathryn Bex

(57) ABSTRACT

This invention relates to an automated device for loading a centrifuge where tubes are presented to the centrifuge via an automated routing system.

4 Claims, 10 Drawing Sheets

AUTOMATED CENTRIFUGE LOADING DEVICE

This application claims the benefit of U.S. Provisional No. 60/053,260 filed Jul. 21, 1997

SCOPE OF THE INVENTION

This invention relates to an automated device for processing sample containers through a device which requires a particular arrangement of these containers. More specifically this invention relates to a robotic device, also called a station, which is capable of transferring test tubes from a device which brings sample to be centrifuged to the vicinity of the centrifuge, arranges them in a balanced fashion in centrifuge sample carriers on an intermediate staging area, loads and unloads the centrifuge, and transfers the processed samples to their originating point, or to a third point or device.

BACKGROUND OF THE INVENTION

Centrifuging is a necessary step in the processing of blood samples in a clinical laboratory setting. Most current clinical tests require that serum or plasma be separated from red blood cells, and other blood debris, before an assay can be run on the sample. Most often this is accomplished by centrifugation, although dialysis- or filtration-type technologies are used in some operations, particularly where only a small quantity of sample is available. But for the most part, centrifugation is an essential preparatory step in the processing and testing of blood samples in a clinical laboratory setting.

Lab automation is becoming a standard in clinical laboratories which do large test volumes. Automation in the large lab context is moving to an assembly-line type operation. Samples are introduced onto an automated sample routing system. Conveyor belt systems are the preferred choice in most automated systems. The system moves test tubes to some predetermined location based on information on the order form associated with that sample which has been fed into the system's control mechanism. At the predetermined stop, the sample tube is put into a holding pattern, an aliquot is removed, and the aliquot is tested for the analyte as per its order form. See for example U.S. Pat. No. 5,623,415 which is incorporated by reference herein in full.

While several automated routing systems are now marketed or are functioning in captive labs, their through-put is often no faster than the preparation and/or loading step. Centrifugation takes 7 to 10 minutes for cycling through a load of tubes, i.e., loading up the centrifuge baskets, spinning down the blood samples, and unloading the processed tubes. Most if not all sample prep steps involving centrifugation is now done prior to loading tubes onto the automated routing system. In that context, where centrifugation is required, the centrifuge is loaded and unloaded manually off-line, then centrifuged sample tubes are loaded onto the routing system. A manual operation requires staffing, requires additional human handling of tubes, and requires decision making as to which tubes to place in which carrier to achieve a balanced load in the centrifuge. A manual operation can be rate limiting and is more expensive than would be an efficient automated robotics system.

Some attempts have been made to automate the centrifugation step. One system is currently being marketed by Coulter® Corporation, Miami, Fla., USA. It uses a 4-stage system to prepare samples. Tubes are loaded into racks in an inlet module; the racks are moved via conveyor to a bar-code reader; then the racks move to a centrifuge module which uses a robotic arm to pick tubes needing centrifugation from the racks, loads them directly into the centrifuge baskets in the centrifuge, and returns them directly to the racks on the conveyor; after which the racks are routed to other processing devices prior to being routed to assay stations. One slow step in this operation is the centrifugation loading and unloading operation. The robotic load/unload operation must remain inactive during the centrifuge's spin cycle; it can not be loading and unloading tubes during the spin cycle since it moves tubes between transport rack and centrifuge tube adaptor in the centrifuge. What is needed is a more efficient system which minimizes the time lost to the overall operation caused by the necessary wait for the centrifuge's spin cycle to be completed. If some operation could be slotted into this down-time, some operation which has to be done in any event, the overall efficiency of the operation could be greatly enhanced. This invention provides such a solution.

SUMMARY OF THE INVENTION

In a first aspect this invention relates to a process for automating the processing of samples through at least one fault-tolerant centrifuge using a device which has a processing station interposed between a tube collection or transport device and a fault-tolerant centrifuge, the station comprising:
  a) a staging area for tube adaptors compatible with the centrifuge;
  b) a dual function tool having:
    i) a tube gripper which can recognize and adapt to tubes of different heights and diameters on the tube collection or transport device and which routes tubes between the tube collection or transport device and the centrifuge adaptors on the staging area; and
    ii) an adaptor gripper capable of transporting adaptors to and from said centrifuge, the process comprising:
      a) under automated control:
        (1) identifying the height and diameter of a tube on the tube collection or transport device;
        (2) selecting a tube which have a pre-set height and diameter;
        (3) gripping and removing the selected tube from the collection or transport device;
        (4) placing the tube in an adaptor on the staging area in a sequence which provides paired adaptors of essentially balanced weight such that when the centrifuge cycles, the weight distribution between the paired adaptors is within the fault tolerance limit of the centrifuge;
        (5) placing the filled or partially filled, balanced, paired adaptors into the centrifuge opposite each other;
        (6) removing adaptors from the centrifuge to the staging area after the spin cycle; and
        (7) picking cycled tubes from the adaptors and placing them on the tube collection or transport device.

It is preferred to carry out the adaptor fill and unload operation during the centrifuge spin cycle.

In a second aspect this invention relates to a robotic device for automating the processing of samples through a fault-tolerant centrifuge, the device comprising:
  a) a tube collection or transport device interfaced with,
  b) a processing station interposed between the tube collection or transport device and at least one fault-tolerant centrifuge and interfaced with c) a fault-tolerant centrifuge, the station having
  i) a staging area for tube adaptors compatible with the centrifuge; and
  ii) a dual function tool having
    a) a tube gripper which
      (1) recognizes and adapts to tubes of different height and diameter on the tube collection or transport device;
      (2) selects tube of only a pre-set height and diameter;
      (3) places tubes in paired adaptors in a balanced fashion;
      (4) routes tubes between the tube collection or transport device and the centrifuge adaptors on the staging area, and vica versa; and
    b) an adaptor gripper capable of transporting adaptors to and from the centrifuge;
    c) an electronic control means for controlling the action of the tool in sequence with the operation of the tube collection or transport device, the placement of tubes in adaptors in a balanced fashion, the transport of adaptors to and from the centrifuge in sequence with the cycling of the centrifuge, and the unloading of processed tubes from adaptors.

DETAILED DESCRIPTION OF THE INVENTION

Figure 1:
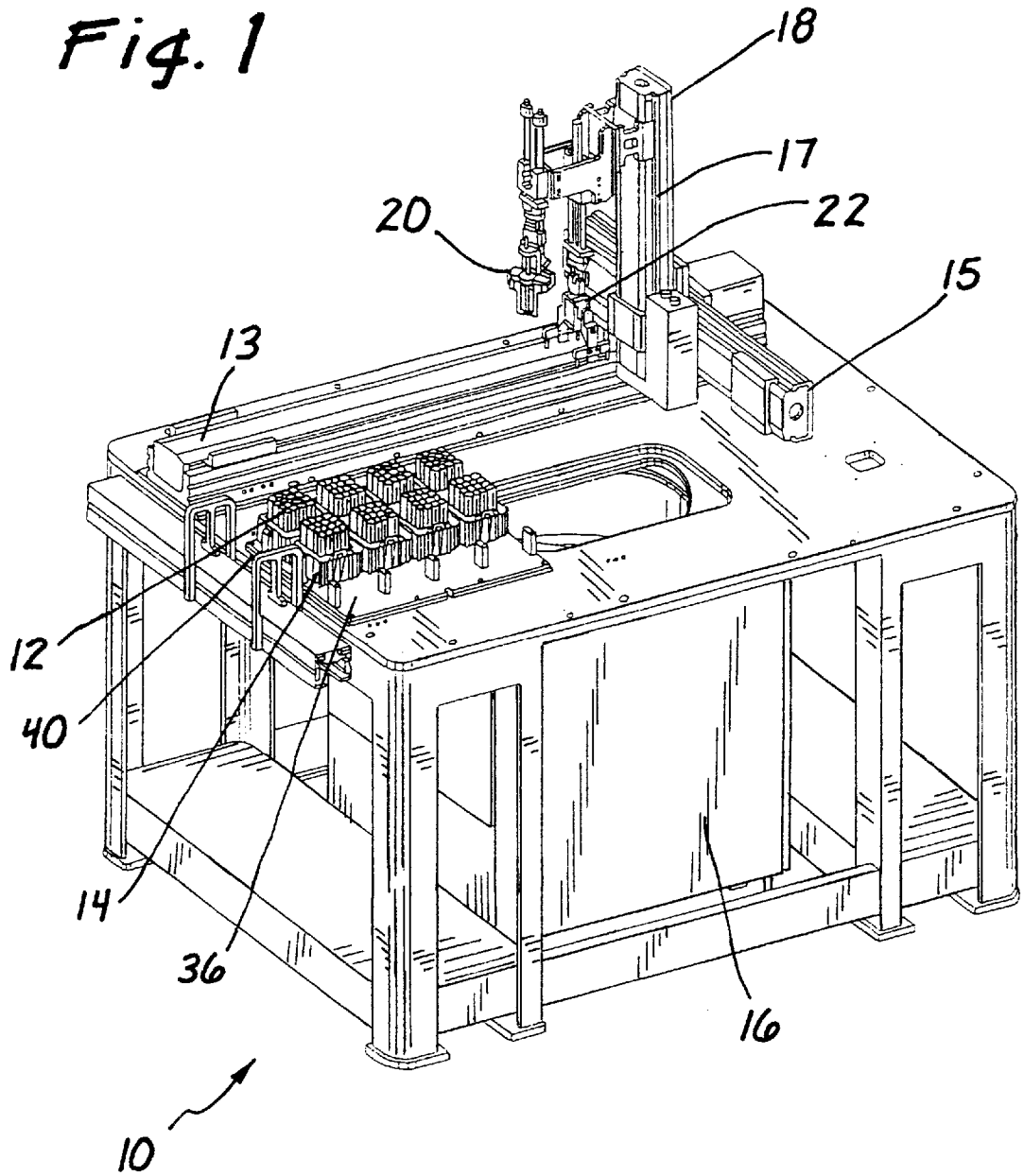
FIG. 1 Elevated frontal view of the device showing tube conveyor, robotic arm, staging area, and centrifuge.
Figure 2A:
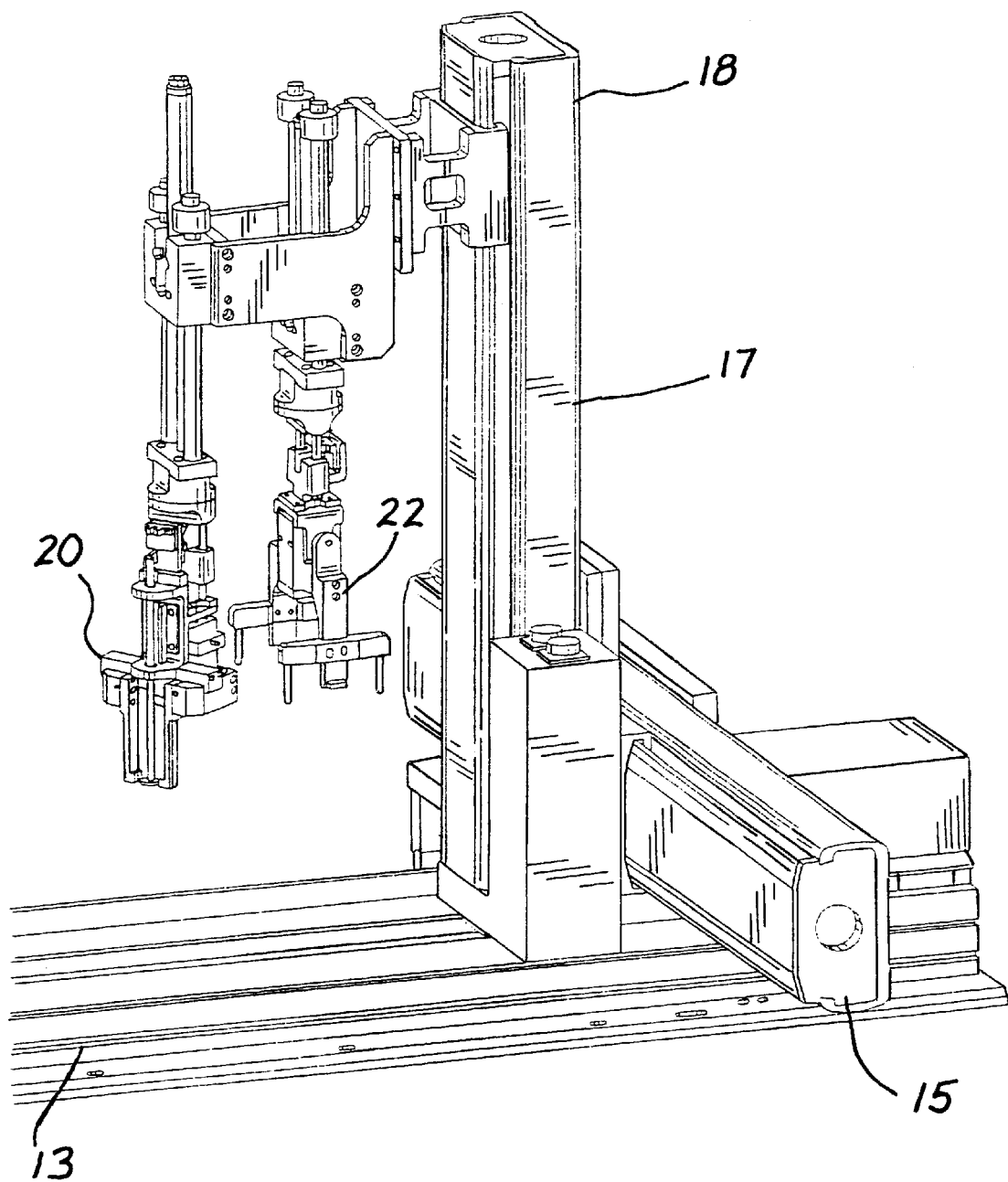
FIG. 2a Frontal view of the robotic arm with adaptor gripper in the up position and tube gripper in the down position, and the arm's transport mechanisms.
Figure 2B:
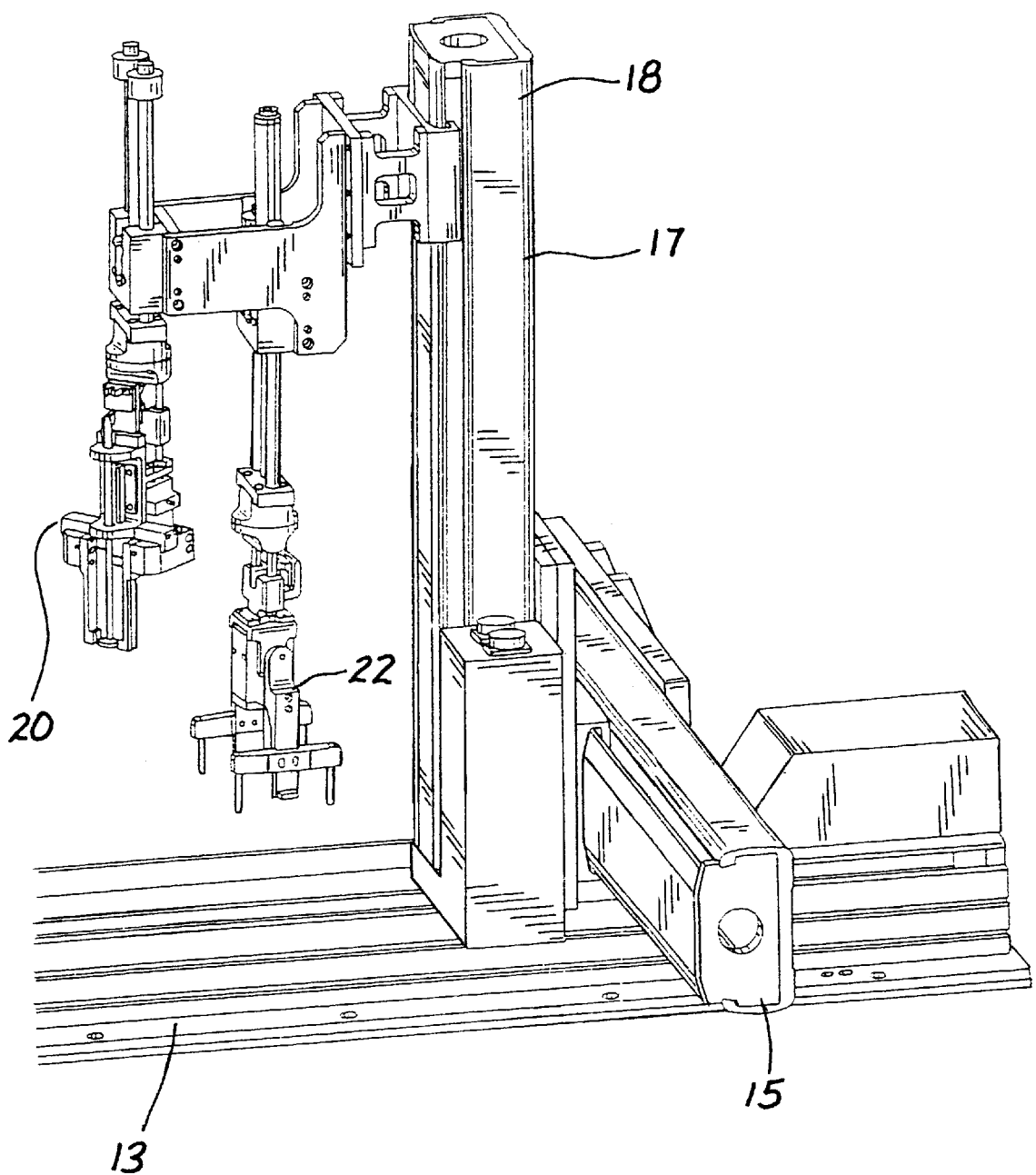
FIG. 2b Frontal view of the robotic arm with tube gripper in the up position and adaptor gripper in the down position, and the arm's transport mechanisms.
Figure 3A:
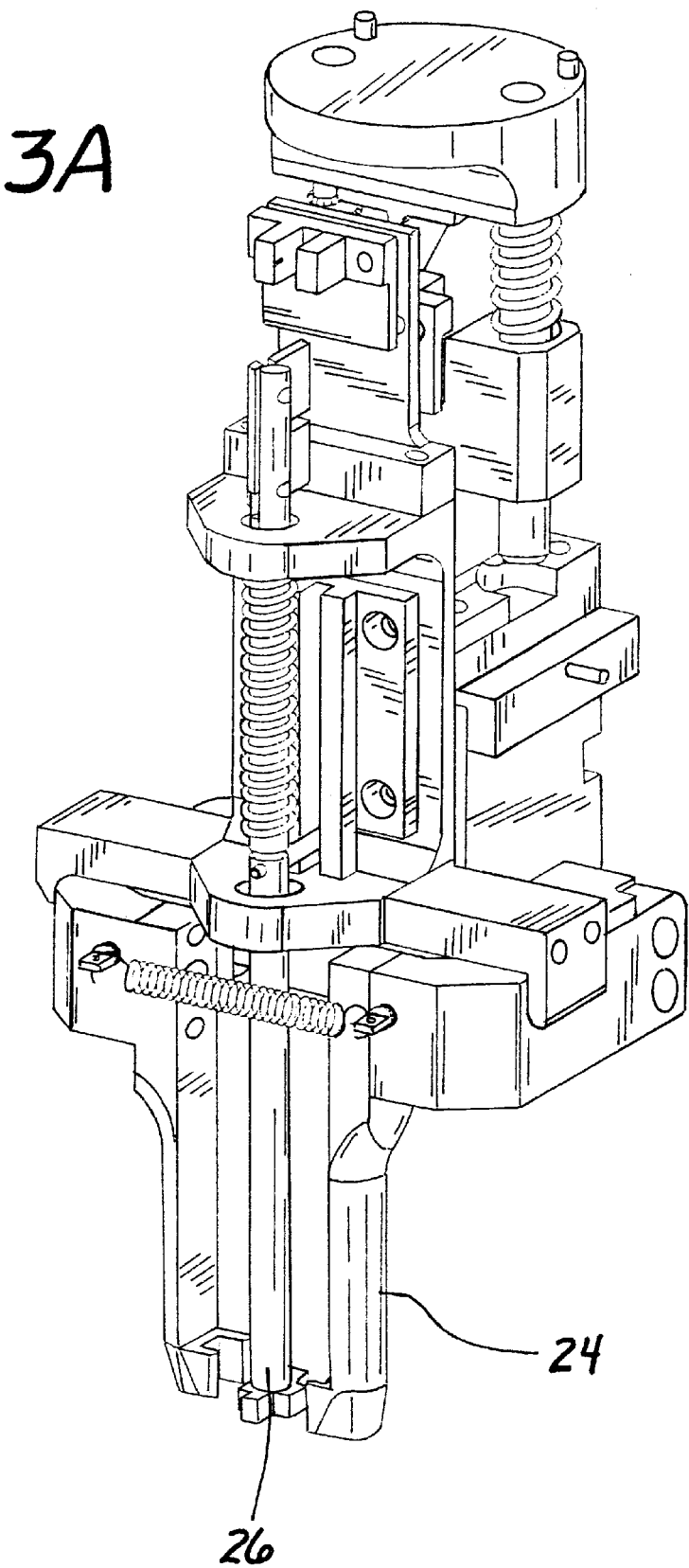
FIG. 3a Frontal view of the tube gripper in the open position.
Figure 3B:
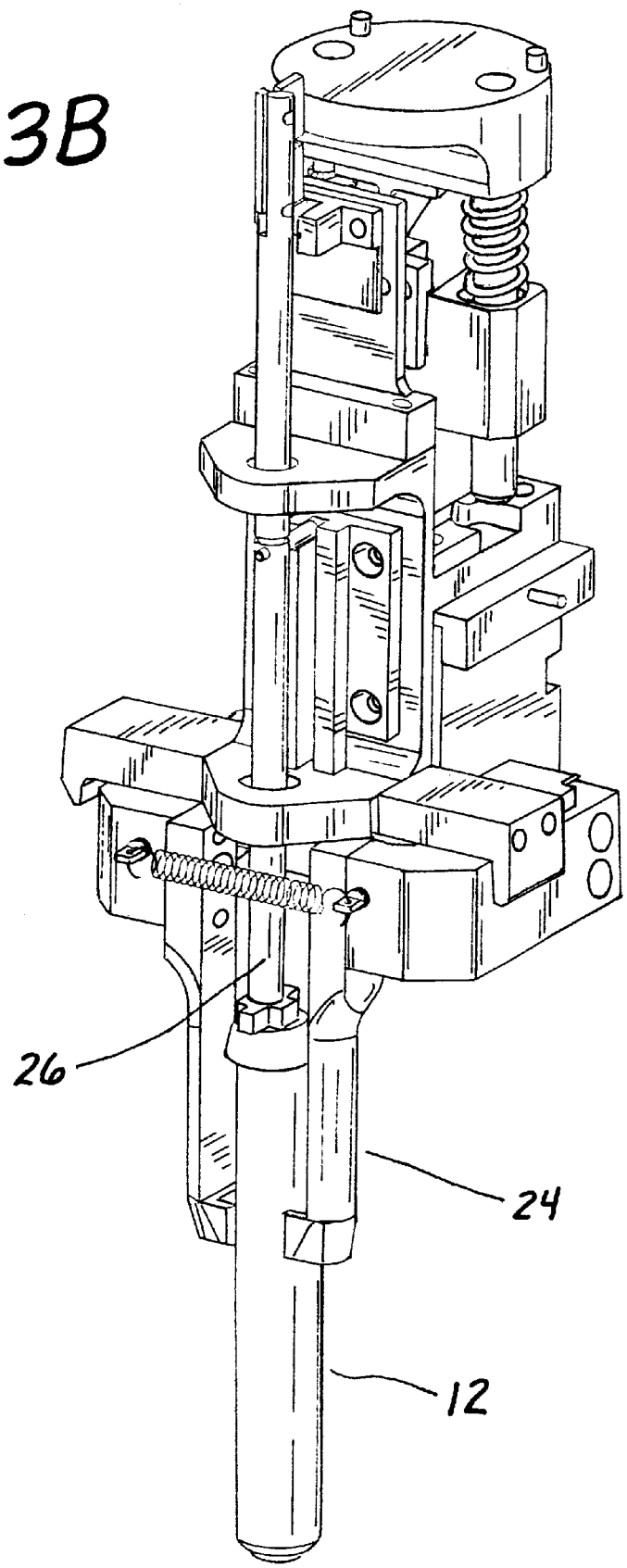
FIG. 3b Frontal view of the tube gripper mechanism in closed position.
Figure 4:
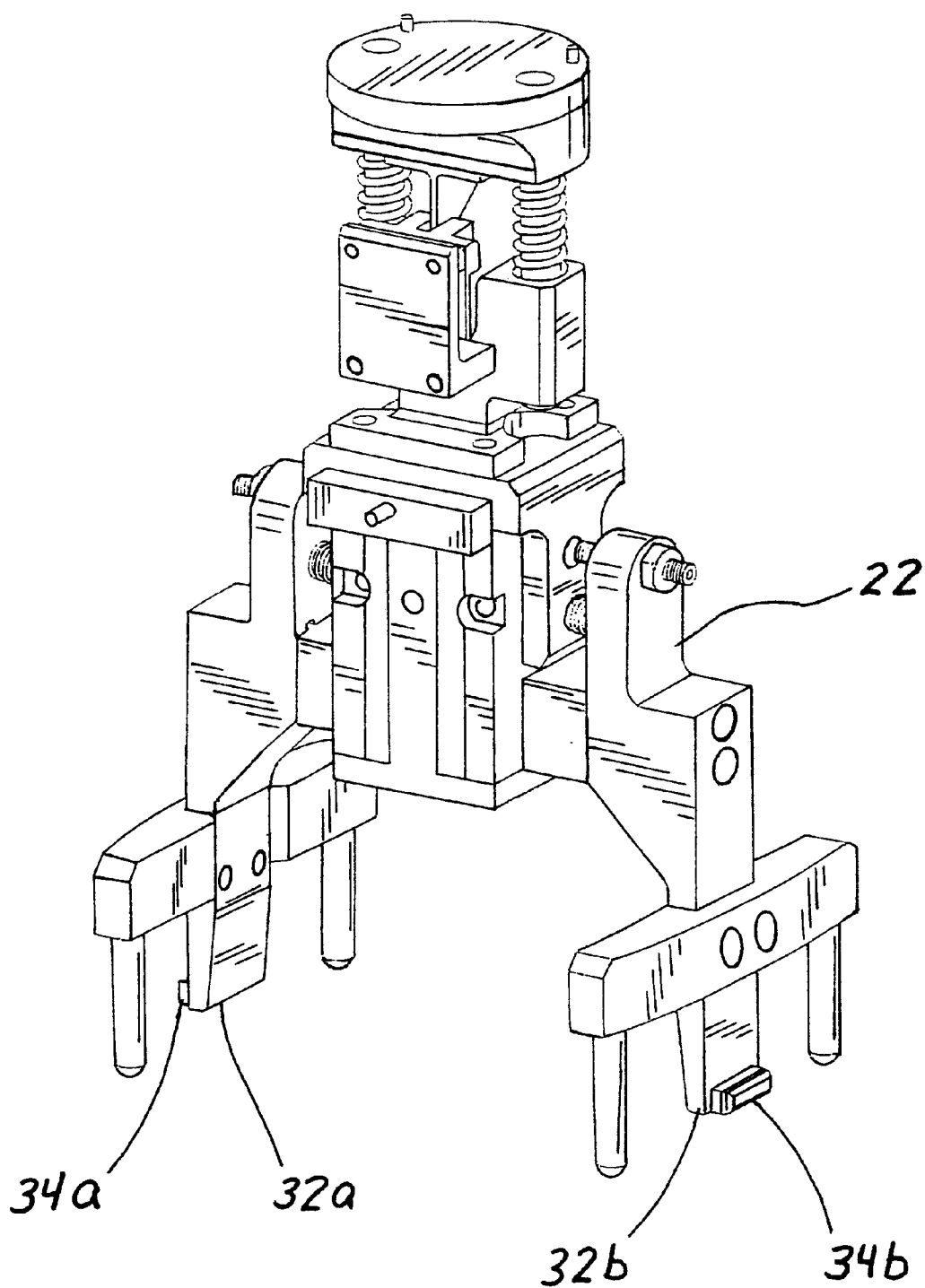
FIG. 4 Frontal view of adaptor gripper without an adaptor.
Figure 5:
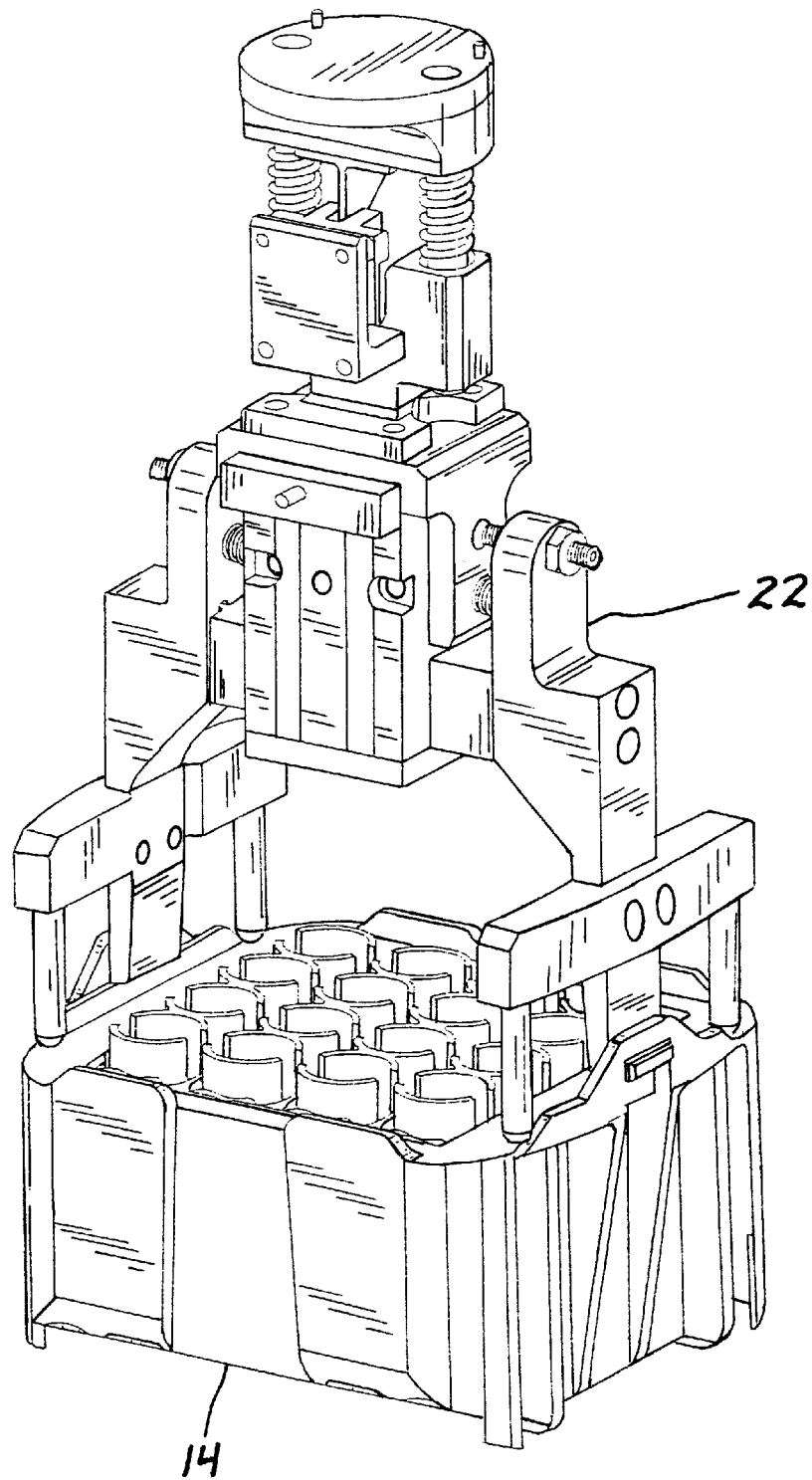
FIG. 5 Frontal view of the adaptor gripper with adaptor.
Figure 6:
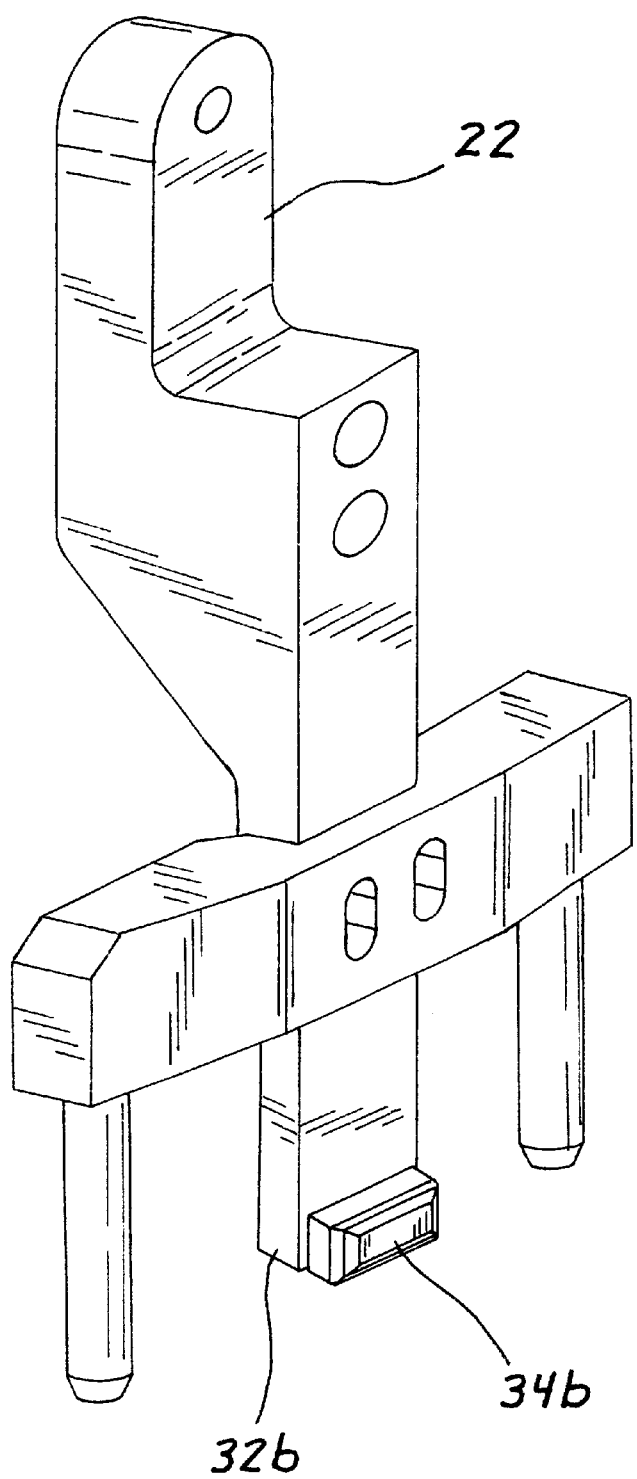
FIG. 6 Detailed view of the adaptor gripper hand with outrigger pins.
Figure 7:
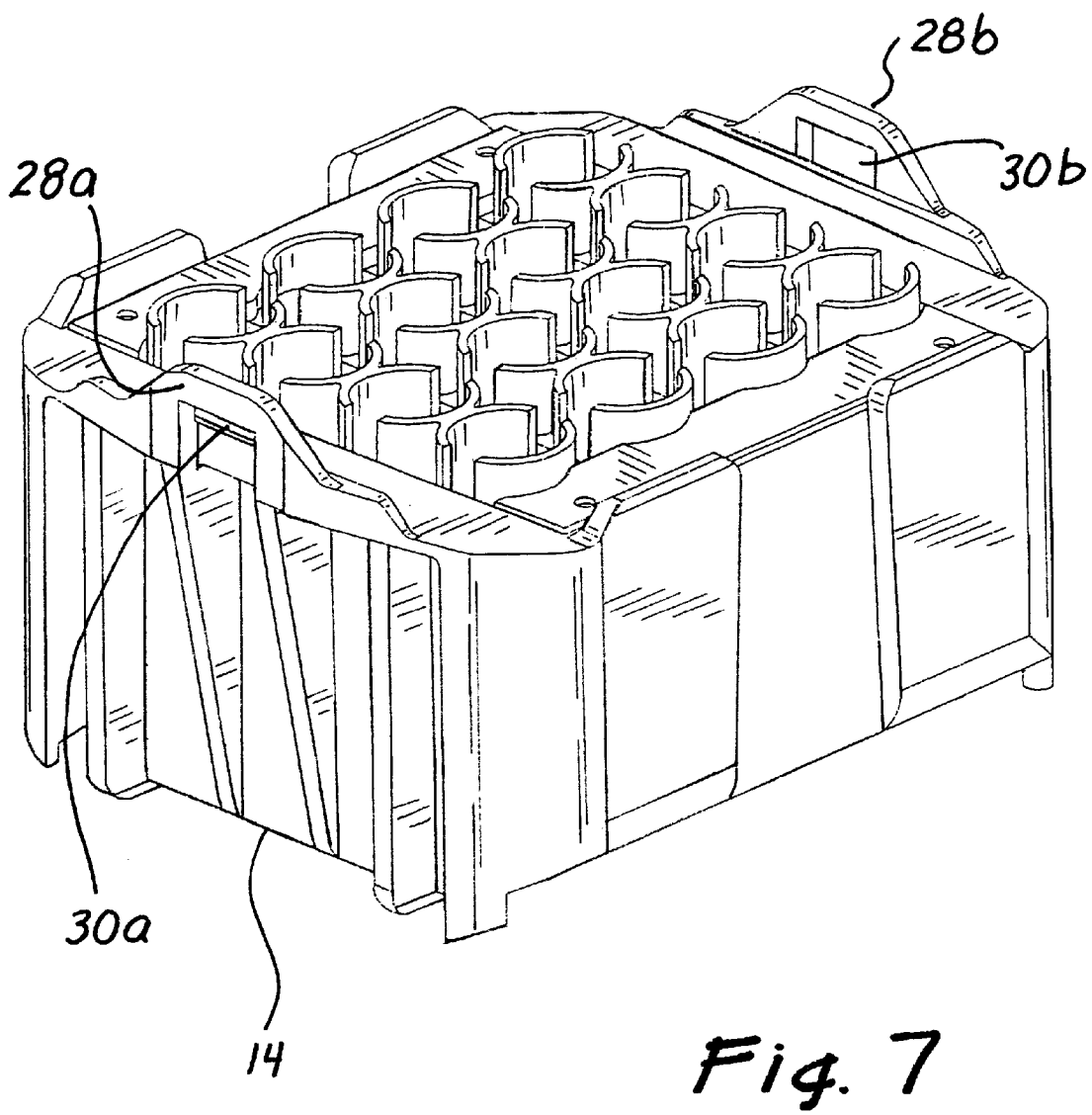
FIG. 7. Top view of a universal adaptor.
Figure 8:
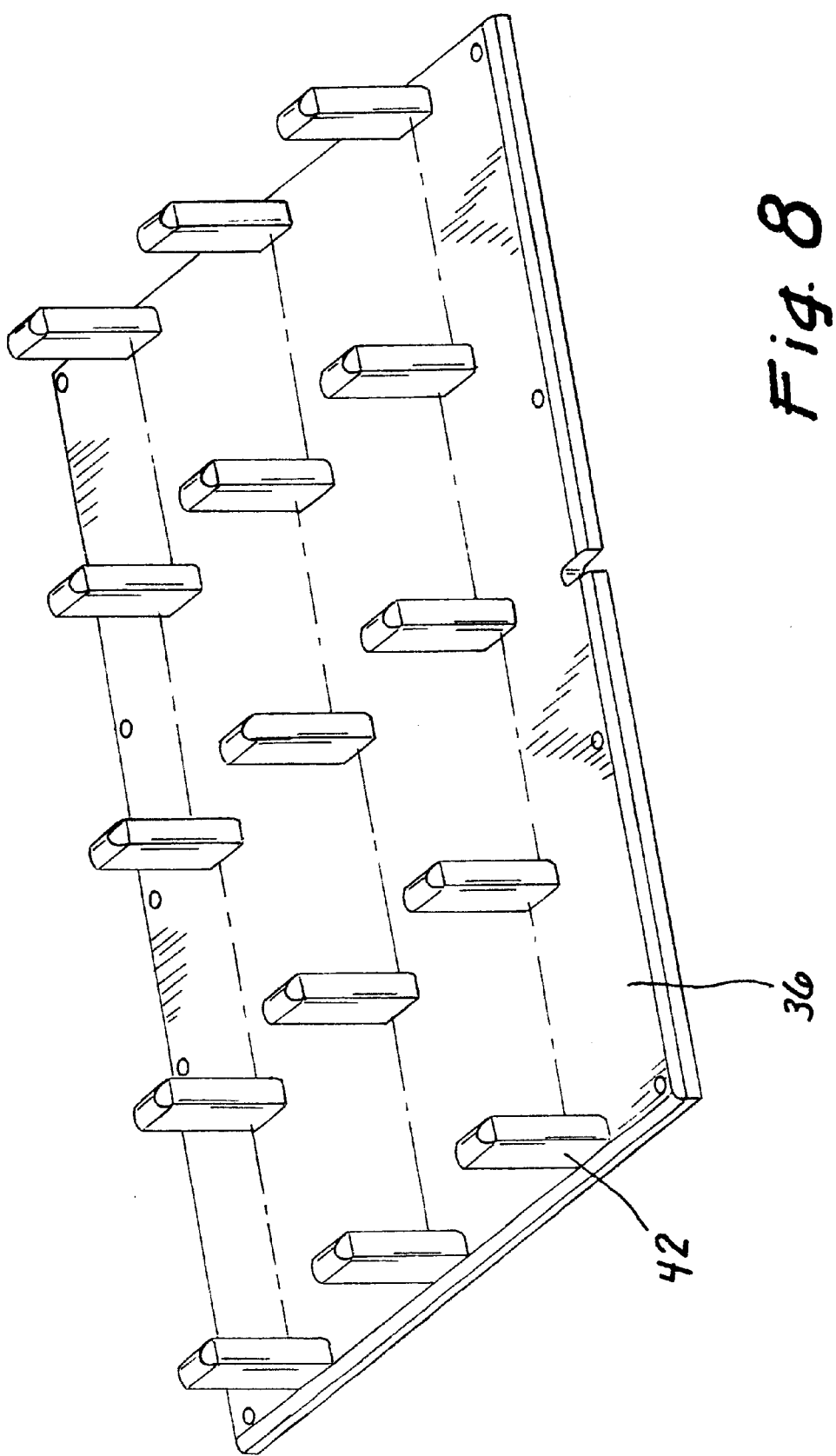
FIG. 8 Top view of the adaptor bed 36 with adaptor sensor array.

In its broadest form, this invention provides a device 10 which can increase the throughput of sample tubes 12 which must be ganged for further processing by picking tubes a collection device, organizing them in a preferred fashion in a carrier, moving the carrier to the work-station or device, returning the carriers to the staging area, and unloading tubes to the original operation See, e.g., U.S. Pat. No. 5,623,415 or to a third site or operation. A specific and preferred operation of this type is the use of this device to pick clinical sample tubes from a conveyor line, place them in centrifuge adaptors 14 so that paired adaptors are balanced, transferring the adaptors from the staging area into and removing them from the centrifuge 16, and returning the tubes to the conveyor line. Filling and unloading adaptors during the spin cycle of the centrifuge 16 provides a substantial time saving operation.

The basic operation of the station is to load tubes from the automated transport system into the tube adaptors in a balanced fashion, and then load adaptors into the centrifuge. After centrifugation, the adaptors are removed from the centrifuge and the individual tubes are returned to the line.

Unless otherwise stated, a PC (586/90 machine) was used to control the operation of this device. Code for controlling the robotics was provided by Yamaha Robotics. The top level operating system used Windows NT 4.0.

The preferred sample tube automated transport system is the device described in U.S. Pat. No. 5,623,415. All specific operations set out below are made with reference to the device described in that patent. But this is merely an exemplary device. This invention can be used with any automated device, or can be used as a stand-alone operation mode, i.e., in a mode where the tubes are presented to it by a static or semi-static device which is used for processing sample tubes,requiring centrifugation.

The robotic arm 18 tube/adaptor transport device is an off-the-shelf 3 axis robot assembly using off-the-shelf parts purchased from Yamaha Motor Co., Ltd, Yamaha Robotics, Broomall, Pa. 19008-0956, specifications as published February, 1995. Any mention of X13; Y15 And Z19 operations noted below refers to the use of this 3 axis robot assembly. Relevant model numbers used in making this assembly are Model #MSA-950, Model #LSHA-450 and Model #LSAV-450. Specifications for the "XYX" configuration are:

X=1050 mm

Z=450 mm

Y=450 mm.

The payload on the Y axis was set at 7 Kg. Tube cycle time was set at between 5–10 seconds.

An example of a fault-tolerant centrifuge is the Accel-Spin™ Centrifuge and AS-3000 Rotor sold by the Spinco Business Center of Beckman Instruments, Inc., Palo Alto, Calif., USA. This device has a 10 gram fault tolerance between paired adaptors.

Overview of Station Operational Requirements

The specific embodiment of this invention is an automated centrifuge station 10 having the following components:

a) A tube router ('interface gate')(not shown,) that allows the station to retrieve individual specimen tubes from a laboratory-wide tube transport system. After centrifugation, the gate allows the tubes to be returned to the transport system for additional processing.

b) Tube 'adaptors' 14, each capable of holding 16 tubes (four rows of four tubes).

c) A centrifuge 16, capable of holding four tube adaptors, ninety degrees apart.

d) A robotic arm 18, capable of
  i) moving tubes 12 between the interface gate and the tube adaptors
  ii) moving tube adaptors into and out of the centrifuge Robotic Tube and Adaptor Device The dual function tool has a tube gripper 20 and an adapter gripper 22 on separate vertical axis. When one gripper is made operational it is lowered and the other gripper is raised to an inactive position; when one is up, the other is always down. Gripping/releasing controls are built into each gripper and each set of controls acts independently.

The preferred tube gripper is a two-finger device with a mandrel 26 positioned between and above the cavity scribed by the two fingers 24. This mandrel is used to sense tube height. The tube gripper is moved to a position where the fingers are on either side of the tube and the mandrel is above the tube and projecting into the cavity scribed by the fingers. The tool then lowers gripper, the mandrel touches the top of the tube and is moved vertically. Sensors on the mandrel interface with sensors on its housing to detect a tube that is either too tall, is within a defined acceptable range, or is too short. If the tube height is within the pre-set acceptable height range, the fingers are activated and close on the tube, and by that operation detect tube diameter. An acceptable tube is then lifted from its holder, the tool is directed to move to a position over an adapter, based on the parameters of the tube then in the gripper, and placed in a one or the other of the paired adaptors in a fashion which results in a balanced load being effected between paired adaptors. If the tube is not acceptable, it is not gripped, and the tool is retracted and sent in search of another tube.

The adaptor gripper in the dual function tool is engineered to grip the adaptor in a manner which provides for lifting and moving adaptors back and forth between the staging area and the rotor spindle in the centrifuge (not shown.) This can be accomplished by a number of means. Herein the universal adaptor was given a set of wings 28a and 28d with rectangular hole 30a and 30b extending vertically above the top plain of the tube holder into which are matched rectangular projections 34a and 34b on the arms 32a and 32b of the adaptor gripper. The gripper arms are moved to a position central to the wings, the holes and projections are aligned, and the arms are moved out causing the arms' projections to insert into the holes of the wings. By this means the adaptor is gripped and manipulated. Preferably included in this adaptor manipulating means (locking device or gripper) is a means for righting adaptors which end up canted at the end of the spin cycle. This righting means can take many shapes and forms, and will necessarily depend on the shape of the device used to secure adaptors to the robotic hand and the shape of the adaptors. The preferred righting means disclosed herein involves two mechanisms, either of which may be used, either together or independently. In one iteration the locking device has a set of equal length fingers extending from the bottom of each side of the gripper hand. Normal gripper operations is to have the arms in the "open", position, i.e., positioned more centrally to the axis of the gripper, so the locking mechanism can be inserted inside the wings of the adaptor, expand and lock up with the wings. In this normal or default position, when the robot moves to secure an adaptor after it has been through the spin cycle, if there is a canted adaptor, one set of these fingers, or "outrigger" posts, will contact the top of one side of a canted adaptor before the other, and as it continues to descend, right the adaptor. A second method was developed to right canted adaptors. The adaptor gripper, rather than remaining in the "open" mode which is the default mode, goes to "closed" mode, the arm descends, causing the bottom of the gripper's outrigger posts on one side of the hand to contact the top of an adaptor, then to continue descending while pushing on the adaptor, until the adaptor is horizontal or essentially horizontal. At that point, the gripper is programmed to lift slightly (if necessary), go to the default "open" mode, reinsert itself fully into the adaptor, and move to the "closed" mode, thus locking up with its wings and gripping the adaptor.

Tube Size Handling Requirement

In a preferred embodiment, the tube handling device must be capable of manipulating tubes of heights from 75 mm to 100 mm. The tube diameter may also vary from 13 mm to 16 mm. With appropriate adaptation, this device can be made to handle a tube of any height and diameter that can be processed by a given size centrifuge.

A universal adaptor was designed that can hold tubes varying in height from 75 mm to 100 mm. The essence of this universal adaptor is the fact that all tubes seat at the same level, leaving the top of the tubes to be at different heights. This was done because the preferred mode of operation was to grip each processable tube at the same height from the bottom of the tube, without regard to its height. This is but one example of how the tube size handling process can be programmed.

Weight Balancing

A centrifuge usually holds four adaptors, located 90 degrees apart. Due to the high centrifugal forces, a pair of adaptors, loaded 180 degrees apart in the centrifuge, must weigh nearly the same or the centrifuge mechanics can be damaged. The maximum allowed imbalance for an adaptor pair is up to about 10 grams, given the current state of the art of centrifuges. A 100 gram tolerant device is currently under development by Beckman Instruments.

To accommodate the imbalance requirement while still allowing maximum throughput, a pair of adaptors are built at the same time. That is, the first arriving tube is placed in adaptor 1, the second tube is placed in adaptor 2, the third tube is placed in which ever adaptor is lighter, the fourth tube is again placed in whichever adaptor is lighter. The weight of a tube is estimated from its height and diameter, numbers detected via gripper sensors and fed back to the system control software. This estimate is made based on the average gross weight for at tube of that diameter, a number which was programmed into the software and correlated with tube height and diameter. In this way, even if a partial load must be centrifuged, the opposing adaptor will weigh the same within the fault limit of the centrifuge. When adaptor 1 and adaptor 2 are filled, the process is repeated with adaptor 3 and adaptor 4. This is the preferred algorithm. An alternative is to use a third adaptor, or a tube holding device, to serve as an intermediate repository so tubes can be shuttled amongst the three adaptors (or two adaptors and the holder) until the operating paired adaptors are in balance. In this operation tubes can be taken from the heavier adaptor and moved to the lighter adaptor, or moved to the intermediate holder. Balance also can be achieved by taking an appropriate sized tube from the intermediate holder and placing it in the appropriate one of the paired adaptors to achieve balance. While it is a preferred operation to place the next tube in the lighter adaptor, that operation is not an essential feature of this invention.

Throughput

A target throughput is as follows:

When a full load is centrifuged, 64 tubes are processed (that is, four adaptors, each holding 16 tubes). The centrifugation time is about 8 minutes. It is permissible to take 1 minute to unload the processed adaptors and replace them with full, unprocessed adaptors. This produces a centrifuge cycle time of 9 minutes, or 6 ⅔ cycles per hour. This means the maximum station capacity is 426 tubes per hour (64 tubes per cycle times 6 ⅔ cycles per hour). The rated throughput is 450 tubes per hour (tube loading/unloading in the adaptor). This is the targeted throughput. It will be appreciated that this is not a limitation on the invention. It is envisioned that it can be operated at a partial capacity, so long as the paired adaptors are balanced. For example a single pair of adaptors can be used, and this pair need not be fully stocked with tubes. In a clinical lab setting, end of day processing often involves less than a full capacity spin cycle.

Factory Host Communication

The system is under the control of the factory control package provided by Yamaha Robotics, called the factory host. The station must be able to accept control commands (such as start-up and shutdown), report status (such as a failed bar code reader), and report the bar code ID of the tubes as they leave the station. A list of supported factory host commands is included below.

Error Detection and Recovery

The station must safely respond to a variety of operating conditions, including

Broken tubes

Jam of a tube against unexpected obstructions

Errors reported by the automated centrifuge controller

Errors reported by the robot controller

No bar-code-read as the tube is attempting to exit the station

Operator activation of a safety device, such as the e-stop button

Power failure

Handling of Partial Loads

Due to the random arrival of work via the transport system, it cannot be guaranteed that a full load of 64 tubes will always arrive in a timely fashion. A way must be provided for the operator (or a built-in wait 'time-out') to force a load and centrifuging of a partial load.

When a partial load is processed, there are not enough empty pucks to remove the full load that was previously processed. This is because the removal of newly arriving tubes creates the empty pucks that are used to hold and ship the previously processed tubes. The handling of partial loads implies a method is available to request empty pucks to facilitate the timely removal of previously processed tubes.

Tube and Adaptor Tracking Requirements

Since the station must be able to gracefully and quickly recover from interruptions in processing (such as power failures, tube jams, e-stop activation, etc.), the station must track the location of all adaptors and tubes as they travel through the station. The tracking information must be frequently written to non-volatile storage (such as a hard disk) to ensure speedy and reliable recovery.

An adaptor "present" sensor is built into the station table. This sensor array configuration is useful in tracking where adaptors are located on the table. It assists with avoiding misplacement of a tube. For example when the sensor is integrated into the devices operational controls, the robotic arm can be programmed to place a tube in an adaptor by having the table sense where an adaptor is located, then direct the arm to place a tube in that adaptor. Also, if for some reason a tube does not release from the adaptor when the arm picks it to return it to the tube collection area or conveyor and the adaptor is lifted, the sensor can be programmed to shut down the system. A sensor can be optical or mechanical, or a combination. Sensor technologies are readily available. It is preferred to use an optical sensor, for example one which is resident in posts used to guide and align adaptors on the station's table, which work from a beam between a source light and a sensor tuned to the frequency of that light. When the beam is broken by an adaptor, the space is read as filled. When the beam is sensed by sensor in the second post, the system control treats the area as empty.

Auto-Calibration

The robotic part of the station must know where to place the tubes and the adaptors. This means a variety of locations must be 'taught' to the station. If the station requires maintenance and a piece of the station must be removed, it is highly desirable that the station be able to continue operation without having to have its locations 're-taught'. To accomplish this, an auto-calibration package must be implemented. This package includes sensors to detect the slight change in position of the robotic locations as well as software to calculate the new locations, based on sensor feedback.

Manual Control of Station

For servicing and manual operator error recovery, the station must provide a way to manually control the following pieces of the machine:

Robot

Centrifuge

Gripper

Interface gate

Any other output bit, such as a bit controlling a safety device

Additionally, for diagnostic and set-up purposes, the station must be able to display its sensors.

User-Friendly Initialization, Shutdown, and Restart Sequences

The start-up, shutdown, and restart of the station (following an error) must be as simple and error-free as possible. This includes the requirement of easy-to-follow operator screens and an easy-to-use control panel.

Simple Installation

A robotic station typically has precision mechanics, precision mounting, and taught points. Since this machine will be installed in hospitals by personnel unfamiliar with robots, the installation must be as automatic as possible. Particular attention should be paid to any requirement to accurately teach points.

Operating Modes

Operating Modes—Steady-State Operation
Handling Short Tubes With "Universal Adaptors"

Currently there is available a universal adaptor (the device which holds the tubes in the centrifuge, also called basket and various other names) that can accommodate any blood sample tube. This section details the cycle steps required when using a universal adaptor. This is the preferred approach, to use an universal adaptor. The invention is not limited to this universal adaptor technology. It is merely illustrative of the invention.

The station consists of 12 adaptor slots on the table (3 rows of 4 slots). 4 of the slots (1 row) have adaptors with tubes waiting to be processed. 4 of the slots (1 row) have adaptors that have been unloaded (adaptors are empty). 4 of the slots (1 row) are empty ('no adaptor' slots), ready to receive the processed adaptors from the centrifuge. 4 adaptors with processed tubes are located in the centrifuge. Generally it is preferred to work with three rows on the staging platform, one row being empty, one row having adaptors which are being filled from the conveyor line, and the other row being a row of apators which contain tubes which have been centrifuged and are being processed back into the automated sample routing device.

The steady-state operation of the station begins with the station in the initial state described below:

On the station table, there are four tube adaptors, designated "in process A, B, C, and D". The four adaptors are fully loaded with 64 tubes (16 tubes per adaptor) waiting to be centrifuged. The slots on the table that hold these adaptors are called the "in process adaptor" slots.

In the centrifuge, there are four tube adaptors, designated "processed A, B, C, and D". The adaptors are full, containing 64 tubes (16 tubes per adaptor) waiting to be returned to the transport line.

On the station table, there are 4 empty tube adaptors. These are called "empty adaptor A" and "empty adaptor B", empty adaptor "C" and empty adaptor "D", and the slots on the table that hold these adaptors are called the "empty adaptor" slots.

There are 4 adaptor slots on the table, that are empty. These are "no adaptor" slots.

The normal, steady-state cycle is as follows:
Adapter Loading Cycle, Universal Adaptor The centrifuge door is automatically opened.

The robot lowers the adaptor tool so that the adaptor fingers are available for use. (The adaptor tool is lowered.)

The robot moves to the centrifuge and removes one of the "processed" adaptors, creating a "no adaptor" slot in the centrifuge.

The "processed" adaptor is placed in a "no adaptor" slot on the machine table.

The robot moves an "in process" adaptor to the "no adaptor" slot in the centrifuge, creating a "no adaptor" slot on the. (4 empty adaptor slots will be created in a different row on the table during each cycle. This row of 4 slots will be used to receive processed adaptors from the centrifuge from the next cycle.)

The centrifuge is rotated 180° so that the next "processed" adaptor is exposed in the door opening.

Steps 1–5 are repeated until the centrifuge contains the 4 adaptors waiting to be processed, and the table has 4 adaptors full of tubes waiting to be returned to the line.

The centrifuge is commanded to begin spinning. It will spin for 8 minutes, and will automatically stop.
Tube Loading Cycle, Universal Adaptor The robot lowers the tube tool so that the tube fingers are available for use. (The adaptor tool is raised as the tube tool is lowered.)

A tube (in a puck) arrives at an interface gate from the transport system.

Using sensors, the robot notes whether the tube is long or short, then picks up the tube and places it into an available position in "empty adaptor A". By removing a tube, an empty puck is created at he interface gate. By noting whether the tube is 'long' or short', the station controller keeps track of the estimated weight of 'adaptor A' and its mate, 'adaptor B'. The gripper sensors can also close on a tube to determine if the tube is 13 mm or 16 mm, which further refines the weight estimate.

The robot moves to one of the "processed" adaptors ("processed adaptor A") and removes a processed tube. The tube is placed in the empty puck at the interface gate, the bar code is read and reported to factory host, and the tube is released back into the transport system. Typically the time to pick up a new tube and replace a processed tube should be about 8 seconds (that is, 7½ tubes per minute "in" and 7½ tubes per minute "out").

Another tube arrives at the interface gate on the transport system.

The robot picks up the tube. Using the running estimated weight of 'adaptor A' and its mate 'adaptor B', the robot places the tube into the lighter of the two adaptor pairs. This will result, on average, in alternating between the two adaptors, although it is possible that two tubes in a row could be placed in the same adaptor. Since the permissible weight imbalance is 10 grams (100 grams with an auto balance centrifuge),and the long and short tube imbalance is only 9 grams, use of this algorithm when work is continually arriving always results in full adaptors that always meet the imbalance specification.

The robot retrieves another "processed" tube from "processed adaptor A' or "processed adaptor B". The tube is placed in the empty puck at the interface gate, Steps 10–15 are repeated until the 4 adaptors that used to be "empty adaptor A", "empty adaptor B", etc. are now full of "in process" tubes, both long and short. The adaptors are renamed "in process adaptor A" and "in process adaptor B", etc. The 64 "processed" tubes (from "processed adaptor A", "processed adaptor B", etc.) have been returned to the line. These adaptors are now renamed "empty adaptor A", "empty adaptor B", "empty adaptor C" and "empty adaptor D".

Step 16 is now repeated using "empty adaptor A", "empty adaptor B", etc. "processed adaptor C", "processed adaptor D", etc. When the empty adaptors are full, they are renamed "in process adaptor C", "in process adaptor D", etc.

The tube transfer cycle detailed in steps 10–17 must be completed during the 8 minute centrifuge spin cycle.

The system is ready to begin with the next adaptor loading cycle, as detailed above.
3.2) Operating Modes—Partial Load of Long Tubes Even if the robot can maintain a load/unload rate of 7½ tubes per minute, there is no guarantee that tubes will arrive from the main laboratory at the full rate. This means there may be times in which the station will either wait for more than 8 minutes to fill the "in process" adaptors, or the "in process" adaptors will be centrifuged even though they are not full of tubes.

When a partial load must be centrifuged, there are modifications required to the steady-state operation detailed in section 3.1. In particular, since it is the arrival of new work that creates the empty pucks used to get rid of the processed work, it is clear that not enough empty pucks are created in the partial load case. The system must ask factory host for empty pucks. The cycle described in section 3.1 is then modified as follows:

When an empty puck arrives at the interface, the robot moves to one of the "processed" adaptors and removes a processed tube. The tube is placed in the empty puck at the interface gate and released back into the transport system.

Step 1 is repeated until all processed tubes have been returned to the transport system. The station will not unload the next batch of centrifuged adaptors until all processed tubes from the previous batch have been returned to the line.
Operating Modes—Initialization Sequence During initialization from a cold start, the system is responsible for the following things:

A user-defined routine is executed. This allows a 'hook' into custom initialization, such as cycling power to a robot if required to reset the robot.

The open/close state of the gripper must be established by gripper sensors.

If a tube is in the gripper, it must be manually removed by the operator after some screen prompts.

The gripper must be opened in preparation for grabbing the first adaptor or tube.

The robot must be homed to establish its initial position.

The centrifuge must be homed to establish its initial position.

The system must establish the state of all the adaptor slots, both on the table and in the centrifuge. In the centrifuge, it does this by moving to each of the adaptor positions and moving the gripper fingers into a position that will trigger the jam detector if an adaptor is present. Adaptors present on the table are checked by optic sensors.

Once the location of all adaptors are known, the operator is shown an image of the machine's derived configuration. The operator can enter correction from an interactive display if there are errors in auto-configuration.

Any pucks currently in the interface gate are allowed to pass out of the system.

The system must 'sign-on' to the factory control package factory host by issuing a SIGNON status message and waiting for a 'startup' command from factory host. It is noted that the initialization includes homing the robot. To ensure safe operation, the order of homing the robot axes must be under user control. For example, it is often required to move the 'z' axis up first (i.e., home 'z' first) before the X or Y axes are moved.

Operating Modes—Restart Sequence

Following recovery from an error, the system must gracefully recover and resume operation with minimal operator intervention. The restart sequence is as follows:

A user-defined routine is executed. This allows a 'hook' into custom restart, such as cycling power to a robot if required to reset the robot.

The open/close state of the gripper must be established by gripper sensors.

If a tube is in the gripper, it must be manually removed by the operator after some screen prompts.

The gripper must be opened in preparation for grabbing the first adaptor or tube.

If needed, the robot must be homed to establish its initial position.

If needed, the centrifuge must be homed to establish its initial position.

The system must establish the state of all the adaptor slots, both on the table and in the centrifuge. It does this by reloading the stored image of the adaptor slots from a disk-based file saved repeatedly during runtime to allow graceful restart.

Once the location of all adaptors are restored from disk, the operator is shown an image of the machine's derived configuration. The operator can enter correction from an interactive display if there are errors in configuration.

The system must establish the state of all the tube positions within the adaptors, both on the frame and in the centrifuge. It does this by reloading the stored image of the tube locations from a disk-based file saved repeatedly during runtime to allow graceful restart.

Any pucks currently in the interface gate are allowed to pass out of the system.

The system must 'sign-on' to the factory control package factory host by issuing a "SIGNON" status message.

Operating Modes—Shutdown Sequence

At the end of a day's production, the system must gracefully shutdown operation with minimal operator intervention. The shutdown sequence is as follows:

The operator initiates the shutdown sequence by hitting the 'shutdown' button on the operator panel.

A user-defined routine is executed. This allows a 'hook' into custom shutdown, such as cycling power to a robot if required to reset the robot.

The system completes the centrifugation of all tubes in the centrifuge, and all tubes 'in process' in adaptors. However, no new work is accepted. If any new work arrives, the tubes are immediately released through the interface gate without processing.

The system calls for empty pucks to return all remaining tubes to the line.

After all tubes have been returned to the line, the system writes an image of the state of the adaptor slots to disk, to speed up the next days' cold-start.

The robot is moved into a 'park' position and deactivated.

The centrifuge is locked in a 'park' position and deactivated.

factory host is sent an "INACTIVE" message, telling then factory software that the centrifuge system has become inactive.

A message is displayed telling the operator it is safe to turn off the system power.

Tube and Adaptor Tracking Requirements

To facilitate a graceful restart sequence in the event of error recovery or power loss, the system software must track certain properties of the adaptors and the tubes, and write this data to non-volatile media to keep the data current. The required tracking information is:

The contents of each adaptor slot, both on the table and in the centrifuge, must be known. The slot categories are:

Slot has an "in process" adaptor, waiting for centrifugation

Slot has a "processed" adaptor, waiting to be reloaded back to the line.

Slot has an empty or partially full adaptor, waiting to be filled with new work.

Slot has no adaptor, and can accommodate an adaptor.

b)Each cavity in the adaptor is marked with the following information:

Cavity has a long, 13 mm diameter tube

Cavity has a long, 16 mm diameter tube

Cavity has a short, 13 mm diameter tube

Cavity has a short, 16 mm diameter tube

Cavity has no tube.

The tube-type must be recorded in order to ensure that the system stays within the weight-imbalance requirements.

During a cold start, and every time the system resumes operation following the opening of the interlocked doors, the following operation will occur to promote proper tube tracking:

The first time a tube is placed into each adaptor on the table, the robot will make a sideways motion, expecting to run into the walls of the adaptor and generate a deliberate 'jam detect'.

If the system fails to detect a collision with the wall of the adaptor, it is assumed that the adaptor has been moved, and the current adaptor slot has no adaptor. This will generate an error message, prompting the operator to re-initialize the station.

If the adaptor's presence is verified by the jam detector, the adaptor is marked 'present' in the station's database, and the robot will not need to verify the adaptor's presence until the next interruption of the door interlocks or the next power-down.

Auto-Calibration of Robotic Points

The system must be able to automatically learn the location of various sites within the work cell if they are moved slightly out of alignment. While point teaching may be required during initial installation of the machine, the typical operator has no ability to re-teach robotic points. A sensor-based system must be devised to allow the robot to learn the following points if they move slightly from their factory installed locations:

The centrifuge adaptor loading point.

The interface gate pick-up point.

The interface gate drop-off point.

The points for each of the adaptor slots on the frame.

The expected sensor to use will be the jam detector. By jamming, moving slightly, and checking again to see if the jam went away, the robot can 'feel' its way into the adaptor slots. Also, the location of the cavities within the adaptors must be automatically known. This will presumably be mathematically known from the origin of the adaptors in their respective slots.

If the points have been grossly moved, such that auto-calibration fails, the system software will provide a way to manually move the robot, probably with the robot teach pendant.

Operator Interface

The operator interface physically consists of a color CRT screen, a custom control panel with some buttons and lights, and a stack light. Most of the detailed error messages and more complicated interactions (such as robotic homing instructions) will be displayed via the CRT. The purpose of the control panel is to provide a simple, "non-intimidating" interface for simple operator interactions, such as "start" and "pause". The stack light provides a quick visual indicator of proper or improper operation that is easily visible from a distance.

6.1) Operator Interface—Control Panel

The control panel consists of the following buttons, each of which has a computer-controlled light attached:

door interlock bypass on/off key-switch moving power-on button (Lit as soon as power is applied)

moving power-off button main power on/off key-switch e-stop button (Lit when the button is depressed, that is, lit when activated).

To start the machine, the operator turns the 'main power' key switch to the 'on' position. The computer and logic receive power, and the computer boots up. When the computer has control, it will do some equipment checks, and instructs the operator to hit the 'moving power' button, to supply power to the centrifuge, the interface gate, and the robot. The computer then begins flashing the 'initialize' button on the CRT (using the mouse). When the operator hits the "initialize" button, the system will perform the initialization sequence detailed in section 3.3. After initialization is complete, the initialize light is turned off, and the "start" button begins to flash on the CRT. Hitting the "start button" causes the machine to begin normal operation, as described in section 3.0. The "start" button light stops flashing and the light becomes steady.

At any time, the operator can hit the "pause" button on the CRT to stop the automatic program sequence. The "start" light turns off, and the "pause" light begins to flash. When in "pause" mode, a display appears on the CRT allowing the control program to be terminated. If the operator selects program termination, a "manual mode" can be entered which allows manual control of the machine from the CRT. This could be used, for example, to release a broken tube from the gripper, or move the robot to a position to allow operator access. If the machine has been placed into manual mode, it must be "initialized" again from the control panel. However, if the automatic mode has never been interrupted, the "pause" can be canceled by hitting the "start" button. This causes the 'pause" light to turn off and the "start" light to be lit.

When the shift is over, the "shutdown" button on the CRT can be hit. This tells the machine that it should finish the work in progress, and then enter the orderly shutdown described in section 3.5. The "shutdown" will flash until shutdown is complete, at which time the "shutdown" light will be steadily lit, and the "start" light will be turned off. When shutdown is complete, moving power and the main computer power can be safely turned off, or the "initialize" button can be hit to begin a re-start.

If the operator notices a partial load of tubes that should be processed immediately, the "partial load" button on the CRT can be hit. Instead of waiting for a full adaptor, the system will load the adaptor as soon as possible. If the system has separate 'long' and 'short' adaptors, there will be two separate "partial load" buttons, one for each tube type.

To stop the robot and centrifuge in an emergency, the 'e-stop' button is pressed. The power to the robot and centrifuge will be turned off, but the computer will remain live so recovery instructions can be given to the operator.

Operator Interface—CRT Display

Operator Interface—CRT Display—Main Runtime Screen

As the machine runs, the adaptor slots keep changing from "in process" to "processed" to "empty" to "no adaptor in this slot". To aid the operator in understanding the machine status, the CRT shows a pictorial representation of the adaptor slots, with the status of the slot displayed in a color code, such as:

"in process"—green (Blink or bright green until full, then steady or pale green) "processed"—red "empty"—white "no adaptor in this slot"—black To further identify the adaptors, the screen image has the following letter identification inside the colored areas:

"I"—in process

"P"—processed

"E"—empty

"N"—no adaptor in this slot

The runtime screen has a message area used to inform the operator of relevant information. For example, after the machine has been powered-up, the message area will say "Hit INITIALIZE button on CRT to initialize the machine". This will help an operator through the start-up and shutdown sequence expected by the machine.

The runtime screen also has an error message area. This area is reserved for error recovery information. A list of errors are given in section 9.

There is a status area on the runtime screen, continuously displaying he following information:

Status state of the factory host communication—connected or not connected

Whether or not a 'startup' message has been received from the factory host.

The station ID, as indicated to the factory host.

The revision level of the software being run

The logic state of the interface gate:

waiting for product waiting to release accumulator tube on robot acknowledge product released from accumulator waiting to release read 1 tube on robot command The logic state of the robot:

waiting for product processing new tube returning old tube to the line loading or unloading adaptors into or out of the centrifuge.

If the operator hits the 'configure' button' on the runtime screen, the operator can access the configuration screen.

If the operator hits the 'pause' button from the CRT, a 'manual mode' button appears on the runtime screen. Hitting the 'manual mode' button causes the system to enter a mode where its components can be individually controlled by the operator. See section 6.2.3.

Operator Interface—CRT Display—Configuration Screen

There are a variety of parameters that affect the operation of the machine that can be adjusted by the operator. These parameters are displayed on the configuration screen. To access this screen, the 'configure' button on the runtime screen is hit. Optionally, the operator can be prompted to enter a password before the configuration screen is activated.

The following parameters can be accessed and changed:

Time to wait for more tubes if full adaptors are not ready when the centrifuge is ready to begin its next cycle. When this time expires, a 'partial load' cycle is triggered.

Robot speed, in per cent

Address of I/O signals, and their corresponding names

Centrifuge spin time and G force, ramp up and ramp down time.

Name of all taught points, and their world coordinates.

Height offsets to 'approach' the taught points. The 'height offset' is the distance above a taught point the robot must move in order to clear the point with a tube in the gripper.

The Station ID to Factory Host

Whether or not factory host character string interaction should be displayed on screen to the operator in a factory host message window.

Whether or not to allow the machine to run without the factory host software running at the same time.

Operator Interface—CRT Display—Manual Control Screen

The manual control screen allows the operator to access to the system in a manual mode. This mode is entered by hitting the "manual mode" button on the runtime screen, which is only available when the system is in a 'pause' state (i.e., the operator has hit 'pause' on the CRT).

The following things can be controlled in manual mode by hitting buttons on the manual mode screen:

the robot the centrifuge door the centrifuge rotor position the gripper pneumatic lines (open/close)

all output bits, including those that control the interface gate

The following things can be monitored in manual mode from the manual mode screen:

the robot position on all axes in physical units the state of all I/O bits the gripper sensor bits: jam detect, full open, full close, close to 13 mm, close to 16 mm Operator Interface—Stack Light The colors and meaning of the stack lights are as follows:

WHITE—Power is applied to the station

GREEN—Normal automatic operation.

RED—System emergency. The station cannot continue without operator intervention. The GREEN light is turned off if the RED light is on.

BLUE—Maintenance—The safety door locks are disabled. the system will run with the doors unlocked and open. This light is included in case the 'maintenance mode' function is put back into the specifications.

YELLOW—The station needs attention, such as clearing a jam at the interface gate, but the station can continue for awhile unattended.

7.0) Interface to Factory Host

The station communicates to factory host via an RS232 serial line from the station controller. Communication is bi-directional.

A list of supported commands are:

Start command

Pause

Continue

Shutdown

Device status reports on line/off-line bar code devices off

Route acknowledge record

Empty puck request

The factory host documentation (available from Yamaha) for the details of the protocol.

8.0) Safety

Safety—Safety doors

The station will have safety doors to prevent the operator from reaching into the station. The doors will have interlock switches, so the station can prevent operator access without disabling the automatic cycle.

Every time the system resumes operation following the opening of the interlocked doors, the following operation will occur to promote proper tube tracking:

The first time a tube is placed into each adaptor, the robot will make a sideways motion, expecting to run into the walls of the adaptor and generate a deliberate 'jam detect'.

If the system fails to detect a collision with the wall of the adaptor, it is assumed that the adaptor has been moved, and the current adaptor slot has no adaptor. This will generate an error message, prompting the operator to re-initialize the station.

If the adaptor's presence is verified by the jam detector, the adaptor is marked 'present' in the station's database, and the robot will not need to verify the adaptor's presence until the next interruption of the door interlocks or the next power-down.

8.2) E-STOP

An emergency stop button (3 locations) is placed on the main frame of the machine. The button will be not be lit under normal operation. When depressed, the light will go on and all power and stored energy (compressed air) will be deactivated within 2 seconds. The robot and the centrifuge will stop moving. The computer will remain powered.

To restart the system, power is first restored by pressing the 'moving power on' button. The operator is prompted on the CRT to run the initialization sequence, followed by the normal runtime sequence.

9.0) Error Recovery Software

The station will automatically handle a wide variety of error conditions. These conditions include:

Tubes on tubes (via a 'jam detect' sensor)
Unexpected jam of the gripper against an object
Power fail To facilitate error recovery, the station will maintain an up-to-date, non-volatile record of the status of the machine on the hard drive. In the event of the need to recover, the non-volatile status file will be retrieved and used to facilitate a graceful re-start, with minimal operator action.

Detailed Error Recovery is Given Below:

9.1) Error: Tube Jam: Tube Can't Fit in 'Adaptor Cavity'

If the tube can't fit in an adaptor cavity, the jam will be detected by the jam sensor. In this case:

The robot moves 'full up' in z, to the 'z' limit.
The red stack light is turned on.
The operator is told to hit 'START' to restart the machine.
The operator is told to clear the jam via screen messages.
The tube is manually removed from the robot gripper by the operator and placed back on the transport system in an empty puck.
The machine resumes normal operation.

9.2) Error: Adapter Jam: Adapter Can't Fit in 'Adaptor Slot'

If an adaptor can't fit in an adaptor slot, the jam will be detected by the jam sensor. In this case:

The robot moves 'full up' in z, to the 'z' limit.
The red stack light is turned on.
The operator is told to hit 'START' to restart the machine.
The operator is told to clear the jam via screen messages.
The adaptor is manually removed from the robot gripper by the operator and placed back on the frame in an empty slot, as shown on the error recovery screen.
The machine resumes normal operation.

9.3) Error: Tube Jam: Tube Can't Fit in Puck During 'Reload'

If the tube can't fit in a puck during 'reload', the jam will be detected by the jam sensor. In this case:

The robot moves 'full up' in z, to the 'z' limit.
The red stack light is turned on.
The operator is told to hit 'START' to restart the machine.
The operator is told to clear the jam via screen messages.
The tube is manually removed from the robot gripper by the operator and placed back in an empty puck in the interface gate.
The machine resumes normal operation.

9.4) Error: NOREAD on Tube Bar Code While Returning Tube to the Line

On a 'NOREAD' on a tube bar code while returning a tube to the line, the station will:

Send factory host a 'NOREAD' message, if desired by lab personnel.
Release the tube back into the transport system.

9.5) Error: Sensor Problem

If a sensor problem is detected, such as a stuck air cylinder, a screen will be displayed to the operator. The sensor must be fixed before automatic operation can continue.

Error: Robot Reported Errors

There are numerous errors that are specific to the robot being used. Any such detected errors will be displayed to the operator, and the system will enter manual mode to allow debug to begin. To restart, the operator must bring the system out of manual mode by hitting the 'automatic run' button, then follow the 'initialize' and 'start' instructions on the CRT.

Error: Centrifuge Reported Errors

There are numerous errors that are specific to the centrifuge. Any such detected errors will be displayed to the operator, and the system will enter manual mode to allow debug to begin. To restart, the operator must bring the system out of manual mode by hitting the 'automatic run' button, then follow the 'initialize' and 'start' instructions on the CRT.

Error: Broken Tube Inside the Centrifuge

As of the writing of this paper, the only approach implemented to detect a broken tube inside the centrifuge is to react to the case when the gripper fingers fail to close on a tube that had been previously placed in a known adaptor cavity.

If this the gripper fails to detect a centrifuge tube that was definitely placed into an adaptor, the error will be displayed to the operator, and the system will enter manual mode to allow debug to begin. The centrifuge must be unlocked, cleaned, and decontaminated. To restart, the operator must bring the system out of manual mode by hitting the 'automatic run' button, then follow the 'initialize' and 'start' instructions on the CRT.

Error: No Tube at Pickup Point

It is possible that the sensors will indicate a tube is present at the pickup point, but when the robot goes to acquire the tube, its gripper sensors fail to detect a tube. In this case:

The robot opens its gripper.
The robot moves 'full up' in z, to the 'z' limit.
The red stack light is turned on.
The operator is told about the error,
Once the operator clears the cause of the problem, the operator should hit 'START' to restart the machine.
The machine resumes normal operation.

10.0) Robotic Tooling

The tooling for tube handling consists of a single set of robotic fingers mounted on the center line of the Z axis of the robot, and located in front of the adaptor tool. The tube tool is held in position vertically by a pneumatic cylinder. The fingers are pneumatically driven. The gripper body is mounted on a rotary ball joint called a 'Unicoupler™', model 4418, Robotic Accessories, Tipp City, Ohio, USA, that can comply in all directions. This gives the tool the ability to safely react to jam conditions. The tool has a sensor to detect displacement away from center, so the station knows of jams. Springs on the tool return the tool to a centered position; stiffer springs may be needed if the weight of the tool is more than the factory-provided springs can accommodate. Springs on the fingers keep the fingers closed in the event of a loss of air pressure. This ensures a tube will not be dropped if the air pressure is lost.

The tooling for adaptor handling consists of a single set of robotic fingers mounted on the center line of the Z axis of the robot, but behind the tube tool. The adaptor tool is also held in position vertically by a pneumatic cylinder. A tool is in a "working" position when it is lowered by its pneumatic cylinder. When the tube tool is lowered the adaptor toll is raised, and vice versa.

The adaptor fingers are pneumatically driven. The gripper body is mounted on a rotary ball joint called a 'Unicoupler™', that can comply in all directions. This gives the tool the ability to safely react to jam conditions. The tool has a sensor to detect displacement away from center, so the station knows of jams. Springs on the tool return the tool to a centered position. Springs on the fingers keep the fingers open, pressed against the adaptor handles, in the event of a loss of air pressure. This ensures an adaptor will not be dropped if the air pressure is lost.

The tooling will be equipped with the following sensors:
Tube jam detect
Tube grip fully open
Tube grip fully closed
Tube fingers closed on 16 mm
Tube fingers closed on 13 mm
Adapter jam detect
Adapter grip fully open
Adapter grip fully closed
Rotator in 'tube handling' position
Rotator in 'adaptor handling' position.
Robotic Tooling: Tooling 'Defaults'

The pneumatic lines must be wired so that the tooling 'defaults' are as follows:

When power fails, the tube gripper enters a spring-loaded 'CLOSED' position. This ensures that a tube will not be dropped.

When power fails, the adaptor gripper enters a spring-loaded 'OPENED' position. This is because the adaptor fingers are brought inside the adaptor, and then opened to engage the handles of the adaptor. By having the adaptor fingers fail in an open position, the station ensures that an adaptor will not be dropped.

When power fails, the tool pneumatic cylinders will loose air pressure and allow the tools to lower, but since the line air pressure will be 0 psig, no downward force can be applied to anything that might be located under the tooling.

11.0) Escapement/Bar Code Reader (Transport System Interface Gate)

While not part of the software, a section must be included about the interface gate to document the expected operation and sensors.

The escapement mechanism is used to capture an individual tube from the transport system and determine its bar code when returning the tube to the line.

The escapement consists of an upstream stop, an accumulator stop, and a downstream/read stop. The 'stops' are pneumatic cylinders that stop the pucks which contain the tubes. When the pucks are stopped by the cylinder rod, the conveyor belt continues to move, slipping under the puck. When the puck is stopped, the robot can pick a tube out of the pick up point, or drop a tube into the 'read position' drop-off point.

The 'downstream/read' stop is slightly more complex. At that stop, a rubber wheel touches the puck, rotating it in front of a bar code reader so the bar code can be determined and reported to factory host before the tube is released back on to the line.

The empty puck is released from the 'accumulator' stop and held in the 'read' stop. After dropping off the 'pick up tube' into an empty adaptor cavity, the robot will pick a 'processed tube' and place it in the empty puck at the read stop. A 'downstream bar code reader' is then used to read the bar code of the processed tube, in order to inform factory host. While the read stop is used to hold the previous empty puck, the 'accumulator' stop is free to acquire the next 'in-process' tube in preparation for the next pick/place cycle.

12.0) Input/Output Signals

While not part of the software, a section must be included about the digital input/output bits to document the expected operation.

The following is a list of the I/O requirements of the station:
Digital Bit INPUT:
  'Upstream stop' extended
  'Upstream stop' retracted
  'Accumulator stop' extended
  'Accumulator stop' retracted
  'Read 1 stop' extended
  'Read 1 stop' retracted
  Safety door interlock engaged
  Puck at accumulator
  Puck at read 1 point
  A tube is at accumulator (tube may be of any type, including too small or too tall)
  Start button pressed
  Pause button pressed
  Initialize button pressed
  Shutdown button pressed
  Partial load button pressed
  Robot X homing limit read-back
  Robot Y homing limit read-back
  Robot Z homing limit read-back
  19–32. Future expansion bits.
Digital Bit Output:
  Upstream stop
  Accumulator stop
  Read 1 stop
  Tube rotator motor power
  Stack light—RED
  Stack light—GREEN
  Stack light—YELLOW
  Stack light—BLUE
  Safety door locks engaged
  10 and 11. The two bits comprising the tool rotator control. Two bits are required
  to ensure tool does not move in the event of power fail.
  12–32. Future expansion bits
Serial Ports:
  Robot controller
  factory host
  Tube bar code reader—at downstream
  Centrifuge controller
  Bit I/O controller
Robot Tool Head Line Input:
  Tube jam detect
  Tube grip fully open
  Tube grip fully closed
  Tube fingers closed on 16 mm
  Tube fingers closed on 13 mm
  Adapter jam detect
  Adapter grip fully open
  Adapter grip fully closed
  Tube tool in 'up' position or 'lowered' position.

Pneumatic Line Control:
  Tube gripper open/close
  Adapter gripper open/close
  Rotator for 'tube/adaptor' handling fingers 13.0) Teaching/Touching-up of Robot Points Robot points will be taught manually, using the controller 'teach' package. The robot can be moved by using screen-based software, or can be moved via the robotic teach pendant.

The following points have to be taught:
  The pickup point of tubes from the accumulator stop.
  The placement point of tubes into the downstream read stop.
  Two points on the base plate that houses the adaptors. All slot coordinates are mathematically derived from the origin of this base plate to avoid having to teach each frame slot. Individual cavity points within the adaptors are calculated from the coordinate frame, and do NOT have to be taught.
  The Centrifuge Adaptor Drop Off Point Also, all 'height offsets' have to be specified. A 'height offset' is the distance above a taught point the robot must move in order to clear the point with a tube in the gripper. Offsets are specified using the configuration package.

Handling of Unsolicited Events

There are a variety of unsolicited status events reported by the robot and the centrifuge controller that must be handled by the centrifuge controller software.

Centrifuge messages:
  Running speed, run time, and rotor position, sent every second.
  Door, door latch, and door motor status, sent every two seconds.
  Open limit switch, closed limit switch, rotor status, sent every two seconds.
  Robot messages:
  Illegal command
  Point data destroyed
  Program destroyed
  Memory destroyed
  Parameter destroyed
  System generation destroyed
  Robot emergency stop on
  Robot interlock on
  Watchdog timer error
  Over current error
  Short detected in a motor cable
  Over temperature detected in a motor
  Axis feedback error
  Power module error
  AC power low
  DC power low Generic Controller Software The above sections document the scope of software specific to the Beckman centrifuge. To implement this software, a software platform must exist that provides the following functionality:

A) machine control
  a) Low level hardware control (bits and serial ports):
    i) serial I/O
      1) serial I/O command set and communications driver
      2) robot control
      3) bar code reader
      4) factory host
      5) centrifuge
    ii) bit I/O controlled by station controller
      digital I/O command set and communications driver
      safety devices
      interface gate
      operator control panel (buttons, lights)
      stack lights
    iii) bit I/O directly controlled by robot
      1) tube jam detector
      2) adaptor jam detector
  b) High level hardware control (devices):
    i) robot
      1) robot command set and communications driver
      2) z-height might involve pneumatic-extended z
      3) robot bit I/O, such as jam detector
    ii) centrifuge
      1) centrifuge command set and communications driver
    iii) interface gate
    iv) bar code reader
    v) supervisory communication (factory host) operator interface
C) system services
  a) configuration
  b) robot teach
  c) calibration
  d) diagnostic
  e) help The exemplification provided above is given for the purpose of illustrating the invention. It is in no way intended to limit the scope of this invention. Reference is made to the claims for what is reserved to the inventors hereunder.

What is claimed is:

1. A process for automating processing of samples through a fault-tolerant centrifuge using a device which has a processing station interposed between a tube collection or transport device and the fault-tolerant centrifuge, the station comprising:
  a) a staging area for tube adaptors which facilitates the loading and unloading of the centrifuge;
  b) a dual function tool having
    i) a tube gripper which recognizes and adapts to tubes of different height and diameter on the tube collection or transport device and which routes tubes between the tube collection or transport device and the centrifuge adaptors; and
    ii) an adaptor gripper capable of transporting adaptors to and from the centrifuge, the process comprising:
      a) picking tubes of different height and diameter from the tube collection or transport device under direction of a system's control mechanism,
      b) placing them in adaptors on the staging area in a sequence which provides paired adaptors of essentially balanced weight such that when a centrifuge cycles, a weight distribution between paired adaptors is within a fault tolerance limit of the centrifuge,
      c) placing the paired adaptors into the centrifuge opposite each other,
      d) removing adaptors from the centrifuge to the staging area after a spin cycle; and
      e) picking cycled tubes from the adaptors and placing them on the tube collection or transport system.

2. A robotic device for automating processing of samples through a fault-tolerant centrifuge, the device comprising:
- a processing station which is interposed between a tube collection or transport device and a fault-tolerant centrifuge, the station having
  - a) a staging area for tube adaptors which facilitates the loading and unloading of the centrifuge; and
  - b) a dual function tool having
    - i) a tube gripper which recognizes and adapts to tubes of different height and diameter on the tube collection or transport device and which routes tubes between the tube collection or transport device and the centrifuge adaptors; and
    - ii) an adaptor gripper capable of transporting adaptors to and from the centrifuge;
- an electronic control means for controlling an action of the dual function tool in sequence with the following: 1) operation of the tube collection or transport device, and 2) placement of tubes in adaptors in a balanced fashion, and 3) transport of adaptors to and from the centrifuge in sequence with cycling of the centrifuge, and 4) unloading of processed tubes from adaptors.

3. A process for automating processing of samples through at least one fault-tolerant centrifuge using a device which has a processing station interposed between a tube collection or transport device and a fault-tolerant centrifuge, the station comprising:
- a) a staging area for tube adaptors which facilitates the loading and unloading of the centrifuge;
- b) a dual function tool having:
  - i) a tube gripper which recognizes and adapts to tubes of different heights and diameters on the tube collection or transport device and which routes tubes between the tube collection or transport device and the centrifuge adaptors on the staging area; and
  - ii) an adaptor gripper capable of transporting adaptors to and from said centrifuge, the process comprising:
    - a) under automated control:
      - (1) identifying the height and diameter of a tube on the tube collection or transport device;
      - (2) selecting a tube which have a pre-set height and diameter;
      - (3) gripping and removing the selected tube from the collection or transport device;
      - (4) placing the tube in an adaptor on the staging area in a sequence which provides paired adaptors of essentially balanced weight such that when the centrifuge cycles, the weight distribution between the paired adaptors is within the fault tolerance limit of the centrifuge;
      - (5) placing the filled or partially filled, balanced, paired adaptors into the centrifuge opposite each other;
      - (6) removing adaptors from the centrifuge to the staging area after the spin cycle; and
      - (7) picking cycled tubes from the adaptors and placing them on the tube collection or transport device.

4. A robotic device for automating processing of samples through a fault-tolerant centrifuge, the device comprising:
- a) a tube collection or transport device interfaced with,
- b) a processing station interposed between the tube collection or transport device and at least one fault-tolerant centrifuge and interfaced with
- c) a fault-tolerant centrifuge, the station having
  - i) a staging area for tube adaptors which facilitates the loading and unloading of the centrifuge; and
  - ii) a dual function tool having
    - a) a tube gripper which
      - (1) recognizes and adapts to tubes of different height and diameter on the tube collection or transport device;
      - (2) selects tube of only a pre-set height and diameter;
      - (3) places tubes in paired adaptors in a balanced fashion;
      - (4) routes tubes between the tube collection or transport device and the centrifuge adaptors on the staging area, and vice versa; and
    - b) an adaptor gripper capable of transporting adaptors to and from the centrifuge;
  - c) an electronic control means for controlling the action of the tool in sequence with the operation of the tube collection or transport device, the placement of tubes in adaptors in a balanced fashion, the transport of adaptors to and from the centrifuge in sequence with the cycling of the centrifuge, and the unloading of processed tubes from adaptors.

* * * * *